United States Patent
Ghosh

(10) Patent No.: US 12,390,647 B2
(45) Date of Patent: Aug. 19, 2025

(54) DETERMINING HEART FAILURE USING DIAGNOSTIC METRICS

(71) Applicant: MEDTRONIC, INC., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/603,376

(22) Filed: Mar. 13, 2024

(65) Prior Publication Data
US 2024/0299753 A1    Sep. 12, 2024

Related U.S. Application Data

(63) Continuation of application No. 15/903,550, filed on Feb. 23, 2018, now abandoned.

(51) Int. Cl.
| | | |
|---|---|---|
| A61N 1/36 | (2006.01) | |
| A61N 1/362 | (2006.01) | |
| A61N 1/365 | (2006.01) | |
| A61N 1/37 | (2006.01) | |
| A61N 1/372 | (2006.01) | |
| A61N 1/375 | (2006.01) | |
| A61N 1/368 | (2006.01) | |

(52) U.S. Cl.
CPC ....... *A61N 1/36578* (2013.01); *A61N 1/3622* (2013.01); *A61N 1/36585* (2013.01); *A61N 1/3702* (2013.01); *A61N 1/37205* (2013.01); *A61N 1/3756* (2013.01); *A61N 1/368* (2013.01)

(58) Field of Classification Search
None
See application file for complete search history.

(56) References Cited

U.S. PATENT DOCUMENTS

| | | |
|---|---|---|
| 5,139,020 A | 8/1992 | Koestner et al. |
| 5,156,154 A | 10/1992 | Valenta, Jr. et al. |
| 5,188,106 A | 2/1993 | Nappholz et al. |
| 5,334,222 A | 8/1994 | Salo et al. |

(Continued)

FOREIGN PATENT DOCUMENTS

| | | |
|---|---|---|
| WO | WO 2016039872 | 3/2016 |
| WO | WO 2016061202 | 4/2016 |

OTHER PUBLICATIONS (PCT/US2019/018033) PCT Search Report and Written Opinion dated May 14, 2019 (12 pages).

(Continued)

*Primary Examiner* — Ankit D Tejani
(74) *Attorney, Agent, or Firm* — Mueting Raasch Group

(57) ABSTRACT

A cardiac pacemaker that delivers cardiac pacing therapy that includes delivering the cardiac pacing therapy from a cardiac pacing device, sensing a pacing event from a plurality of electrodes of the pacing device, and sensing an electromechanical signal from an electromechanical sensor of the pacing device. A pre-ejection period is determined in response to the sensed electromechanical signal, and a left ventricular ejection time is determined in response to the sensed electromechanical signal. The pacemaker device performs one or both of adjusting a pacing parameter setting and generating an alert in response to the determined pre-ejection period and the determined left ventricular ejection time.

20 Claims, 8 Drawing Sheets

(56) References Cited

U.S. PATENT DOCUMENTS

| | | |
|---|---|---|
| 5,584,868 A | 12/1996 | Salo et al. |
| 5,924,975 A | 7/1999 | Goldowsky |
| 6,959,214 B2 | 10/2005 | Pape et al. |
| 6,978,184 B1 | 12/2005 | Marcus et al. |
| 7,174,203 B2 | 2/2007 | Arand et al. |
| 7,494,459 B2 | 2/2009 | Anstadt et al. |
| 7,569,020 B2 | 8/2009 | Noren et al. |
| 7,883,469 B2 | 2/2011 | Lippert et al. |
| 7,904,158 B2 | 3/2011 | Stegemann et al. |
| 7,908,005 B2 | 3/2011 | Hedberg et al. |
| 7,985,185 B2 | 7/2011 | De Voir et al. |
| 7,988,614 B2 | 8/2011 | Ben Shalom |
| 8,019,409 B2 | 9/2011 | Rosenberg et al. |
| 8,048,001 B2 | 11/2011 | Patangay et al. |
| 8,112,150 B2 | 2/2012 | Naqvi et al. |
| 8,175,693 B2 | 5/2012 | Rosenberg et al. |
| 8,285,373 B2 | 10/2012 | Ternes et al. |
| 8,301,241 B2 | 10/2012 | Ternes et al. |
| 8,321,017 B2 | 11/2012 | Wenzel et al. |
| 8,364,263 B2 | 1/2013 | Patangay |
| 8,403,860 B2 | 3/2013 | Patangay et al. |
| 8,515,534 B2 | 8/2013 | Ternes et al. |
| 8,588,906 B2 | 11/2013 | Ternes et al. |
| 8,600,487 B2 | 12/2013 | Soriano et al. |
| 8,617,082 B2 | 12/2013 | Zhang et al. |
| 8,620,432 B2 | 12/2013 | Hedberg et al. |
| 8,626,281 B2 | 1/2014 | Ternes et al. |
| 8,700,146 B2 | 4/2014 | Ternes et al. |
| 8,712,519 B1 | 4/2014 | Panescu et al. |
| 8,831,705 B2 | 9/2014 | Dobak |
| 8,862,226 B2 | 10/2014 | Ternes et al. |
| 8,934,970 B2 | 1/2015 | Ternes et al. |
| 8,942,799 B2 | 1/2015 | Ternes et al. |
| 8,951,205 B2 | 2/2015 | Patangay et al. |
| 9,220,903 B2 | 12/2015 | Naqvi et al. |
| 9,381,358 B2 | 7/2016 | Ternes et al. |
| 9,492,138 B2 | 11/2016 | Kapoor |
| 9,630,014 B2 | 4/2017 | Averina et al. |
| 9,687,656 B2 | 6/2017 | Wenzel et al. |
| 9,855,317 B2 | 1/2018 | Bright |
| 9,867,987 B2 | 1/2018 | Ternes et al. |
| 2003/0100925 A1 | 5/2003 | Pape et al. |
| 2004/0267086 A1 | 12/2004 | Anstadt et al. |
| 2005/0027323 A1 | 2/2005 | Mulligan et al. |
| 2005/0234289 A1 | 10/2005 | Anstadt et al. |
| 2006/0095085 A1 | 5/2006 | Marcus et al. |
| 2006/0106322 A1 | 5/2006 | Arand et al. |
| 2006/0142634 A1 | 6/2006 | Anstadt et al. |
| 2006/0167334 A1 | 7/2006 | Anstadt et al. |
| 2006/0190045 A1 | 8/2006 | Marcus et al. |
| 2006/0211909 A1 | 9/2006 | Anstadt et al. |
| 2006/0247702 A1 | 11/2006 | Stegemann et al. |
| 2007/0055170 A1 | 3/2007 | Lippert et al. |
| 2007/0066913 A1 | 3/2007 | Patangay et al. |
| 2007/0293771 A1 | 12/2007 | Noren et al. |
| 2008/0021336 A1 | 1/2008 | Dobak, III |
| 2008/0103399 A1* | 5/2008 | Patangay ................ A61B 7/04 600/508 |
| 2008/0119749 A1 | 5/2008 | Haro et al. |
| 2008/0214888 A1 | 9/2008 | Ben Shalom |
| 2009/0287269 A1 | 11/2009 | Hedberg et al. |
| 2009/0299203 A1 | 12/2009 | De Voir et al. |
| 2009/0306732 A1 | 12/2009 | Rosenberg et al. |
| 2010/0152547 A1 | 6/2010 | Sterling et al. |
| 2010/0228311 A1 | 9/2010 | Naqvi et al. |
| 2011/0009754 A1 | 1/2011 | Wenzel et al. |
| 2011/0009755 A1 | 1/2011 | Wenzel et al. |
| 2011/0015702 A1 | 1/2011 | Ternes et al. |
| 2011/0015703 A1 | 1/2011 | Ternes et al. |
| 2011/0015704 A1 | 1/2011 | Ternes et al. |
| 2011/0034812 A1 | 2/2011 | Patangay et al. |
| 2011/0040345 A1 | 2/2011 | Wenzel et al. |
| 2011/0160790 A1 | 6/2011 | Stegemann et al. |
| 2011/0208077 A1 | 8/2011 | Soriano et al. |
| 2011/0295137 A1 | 12/2011 | Rosenberg et al. |
| 2012/0004564 A1 | 1/2012 | Dobak, III |
| 2012/0004700 A1 | 1/2012 | Hedberg et al. |
| 2012/0041317 A1 | 2/2012 | Patangay et al. |
| 2012/0296228 A1 | 11/2012 | Zhang et al. |
| 2013/0023956 A1 | 1/2013 | Ternes et al. |
| 2013/0023957 A1 | 1/2013 | Ternes et al. |
| 2013/0137997 A1 | 5/2013 | Patangay et al. |
| 2013/0296960 A1 | 11/2013 | Wenzel et al. |
| 2013/0331904 A1 | 12/2013 | Ternes et al. |
| 2014/0052209 A1 | 2/2014 | Ternes et al. |
| 2014/0094875 A1 | 4/2014 | Ternes et al. |
| 2014/0163664 A1 | 6/2014 | Goldsmith |
| 2014/0222115 A1 | 8/2014 | Ternes et al. |
| 2014/0257070 A1 | 9/2014 | Blomqvist et al. |
| 2014/0275925 A1* | 9/2014 | Thakur ................ A61N 1/3614 600/377 |
| 2014/0323891 A1 | 10/2014 | Sterling et al. |
| 2015/0065814 A1 | 3/2015 | Kapoor |
| 2015/0126886 A1 | 5/2015 | Patangay et al. |
| 2015/0127067 A1 | 5/2015 | Ternes et al. |
| 2015/0165211 A1 | 6/2015 | Naqvi et al. |
| 2015/0343223 A1 | 12/2015 | Thakur |
| 2016/0001088 A1 | 1/2016 | Averina et al. |
| 2016/0023000 A1 | 1/2016 | Cho |
| 2016/0106986 A1 | 4/2016 | An |
| 2016/0158280 A1 | 6/2016 | Dobson |
| 2016/0166598 A1 | 6/2016 | Dobson |
| 2016/0271161 A1 | 9/2016 | Dobson |
| 2016/0303377 A1 | 10/2016 | Ternes et al. |
| 2016/0317621 A1 | 11/2016 | Bright |
| 2016/0317816 A1 | 11/2016 | Winter et al. |
| 2016/0361041 A1 | 12/2016 | Barsimantov et al. |
| 2017/0001011 A1 | 1/2017 | An et al. |
| 2017/0021175 A1 | 1/2017 | Yu et al. |
| 2017/0032095 A1 | 2/2017 | Kadooka |
| 2017/0049339 A1 | 2/2017 | Kapoor |
| 2017/0113052 A1 | 4/2017 | An et al. |
| 2017/0238847 A1 | 8/2017 | Inan et al. |
| 2017/0281960 A1 | 10/2017 | Averina et al. |
| 2017/0312516 A1* | 11/2017 | Jackson ................ A61N 1/3962 |
| 2017/0348528 A1 | 12/2017 | Yu et al. |

OTHER PUBLICATIONS

Office Action issued in China for Application No. 201980014821.1 dated December 24, 2024 (16 pages). English translation included.

* cited by examiner

DETERMINING HEART FAILURE USING DIAGNOSTIC METRICS

This application is a continuation of U.S. patent application Ser. No. 15/903,550, filed Feb. 23, 2018, the disclosure of which is incorporated herein by reference in its entirety.

The disclosure herein relates to systems and methods for evaluation and adjustment of delivery of a pacing therapy by an implantable cardiac pacing device.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Leadless pacemakers are used to sense electrical activity and/or deliver therapeutic pacing pulses to the heart. For some patients, one atrial pacemaker may be used in one atrium of the heart. In other patients, multiple leadless pacemakers may be used in at least one atrium and at least one ventricle of the heart. Each leadless pacemaker device typically includes two or more electrodes on its outer housing to deliver therapeutic electrical pulses and/or sense intrinsic depolarizations of the heart. Each leadless pacemaker may be positioned within a chamber of the heart and, in some examples, may be anchored to a wall of the heart via a fixation mechanism.

Patients with heart failure are often treated with cardiac resynchronization pacing therapy delivered by a pacing device to synchronize contraction/relaxation of a heart that has become asynchronous. It is typically advantageous that parameters associated with the delivered pacing therapy for addressing instances of dyssynchrony of the heart be adjusted in order to manage better outcomes for heart failure patients. In addition, heart failure diagnostics and management are critical for managing delivery of cardiac resynchronization therapy.

SUMMARY

A leadless pacing device may include an integrated electromechanical sensor, such as an accelerometer, whose signal can be representative of various mechanical events that occur during the contraction/relaxation cycle of a ventricle of the patient's heart. The time-intervals between these various mechanical events are reflective of cardiac mechanical function and may potentially be used as diagnostic metrics for cardiac dyssynchrony. The present disclosure relates to an automated algorithm which can determine certain relevant time-intervals from the accelerometer signal on a beat-by-beat basis. The data may be incorporated in device diagnostics as markers of cardiac mechanical function presented, for example, as a trend-chart over time. If the markers indicate values of the metrics above or below certain thresholds consistently over a period of time, the device may transmit an alert to the clinician. The data may be also used by the device to adjust pacing therapy in patients with a leadless pacing device positioned within the left ventricle for delivering closed loop resynchronization pacing.

As a result, the present disclosure may address parameters that can be used for managing heart failure in patients to adjust pacing therapy for desired outcomes. In this way, the accelerometer signal of the leadless pacing device provides metrics for heart failure diagnostics and heart failure management. The metrics may also be utilized for adjusting device therapy parameters in a closed loop fashion for optimal cardiac resynchronization.

The exemplary system, device and methods described herein involve determining relevant timing parameters reflecting different intervals of mechanical events that occur during the cardiac cycle and that are sensed by an activity sensor, such as an accelerometer, located within a leadless pacing device. In one example, the leadless pacing device may be positioned within one or more chambers of a patient's heart, such as within the left ventricle of the patient, for example. The timing parameters may be determined when the pacing device determines that both the heart rate and heart rhythm are regular and are not associated with the occurrence of a tachycardia event, such as when the heart rate is less than 100 beats-per-minute (bpm), for example.

Based upon the occurrence of either a sensed ventricular event or a paced ventricular event, or sensed ventricular beat, the pacing device may determine a window of an accelerometer signal that extends, relative to the ventricular event for a period of time, such as approximately 260 ms for example. A first peak of a rectified slope of the accelerometer signal ($|d(accelerometer)/dt|$) within the window is determined, and the timing of the first peak of the rectified slope corresponds to a surrogate of the time indicative of early systole, i.e., early contraction of the ventricle. A second peak of the accelerometer signal is also determined within a window that begins 200 ms after the ventricular event and ends 600 ms after the ventricular event. The second peak serves as a fiducial indicative of the end of systole.

The time period extending from the ventricular event to the first peak is identified as a surrogate measurement of a pre-ejection period (PEP) for the corresponding cardiac cycle, which is typically longer for failing/asynchronous heart function. The time period extending from the first peak to the second peak is identified as a surrogate measurement of an LV ejection time (LVET) for the corresponding cardiac cycle, which is typically longer during normal synchronized pump function and shorter for failing hearts. A ratio $r=PEP/LVET$ may be determined as an indicator of overall cardiac function, with a PEP/LVET having a greater value being associated with higher dyssynchrony and reduced efficiency in the pumping of the heart.

In one example, the pacing device may periodically or continuously monitor these data on a cycle by cycle basis and generate a trend plot over time showing how the three parameters, PEP, LVET and PEP/LVET vary. In another example, worsening heart failure may be determined to be occurring if two or more of the following occur:

i) PEP increases by a certain threshold over the last five days, such as a greater than 20% increase, for example, or increases above a predetermined threshold value, such as 400 ms for example.

ii) LVET decreases by a certain threshold over the last five days, such as a greater than 20% decrease, for example, or decreases below a predetermined threshold value, such as 150 ms for example.

iii) the ratio $r=PEP/LVET$ increases by a predetermined threshold over the last five days, such as an average increase greater than 20% for example, or increases above a predetermined threshold value, such as 0.5 for example.

In one example, once worsening heart failure is determined, an alert may be generated by the pacing device. In another example, the pacing device may adjust pacing parameters, such as an AV delay, or a pacing rate for example, resulting in improved synchronization of markers of dyssynchrony, such as PEP increasing or the ratio of PEP/LVET increasing. In another example the pacing device may continue to auto-tune AV delays (i.e., either decreasing or increasing the AV-delay) on a cycle-by-cycle basis to bring the parameter values within certain thresholds as indicated by the markers of dyssynchrony, PEP, LVET and the ratio of PEP/LVET.

In at least one embodiment, a method of delivering a cardiac pacing therapy may comprise delivering the cardiac pacing therapy from a cardiac pacing device; sensing a pacing event from a plurality of electrodes of the pacing device; sensing an electromechanical signal from an electromechanical sensor of the pacing device; determining a pre-ejection period in response to the sensed electromechanical signal; determining a left ventricular ejection time in response to the sensed electromechanical signal; and performing one or both of adjusting a pacing parameter setting and generating an alert in response to the determined pre-ejection period and the determined left ventricular ejection time.

In at least one embodiment, a cardiac pacing device for delivering a cardiac therapy may include one or more electrodes for sensing a cardiac event and delivering the pacing therapy; a sensor for sensing an electromechanical signal; and a processor configured to determine a pre-ejection period in response to the sensed electromechanical signal, determine a left ventricular ejection time in response to the sensed electromechanical signal, and perform one or both of adjusting a pacing parameter setting and generating an alert in response to the determined pre-ejection period and the determined left ventricular ejection time.

In at least one embodiment, an exemplary system may include non-transitory computer readable medium storing instructions which cause a cardiac medical device to perform a method comprising: delivering the cardiac pacing therapy from a cardiac pacing device; sensing a pacing event from a plurality of electrodes of the pacing device; sensing an electromechanical signal from an electromechanical sensor of the pacing device; determining a pre-ejection period in response to the sensed electromechanical signal; determining a left ventricular ejection time in response to the sensed electromechanical signal; and performing one or both of adjusting a pacing parameter setting and generating an alert in response to the determined pre-ejection period and the determined left ventricular ejection time.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
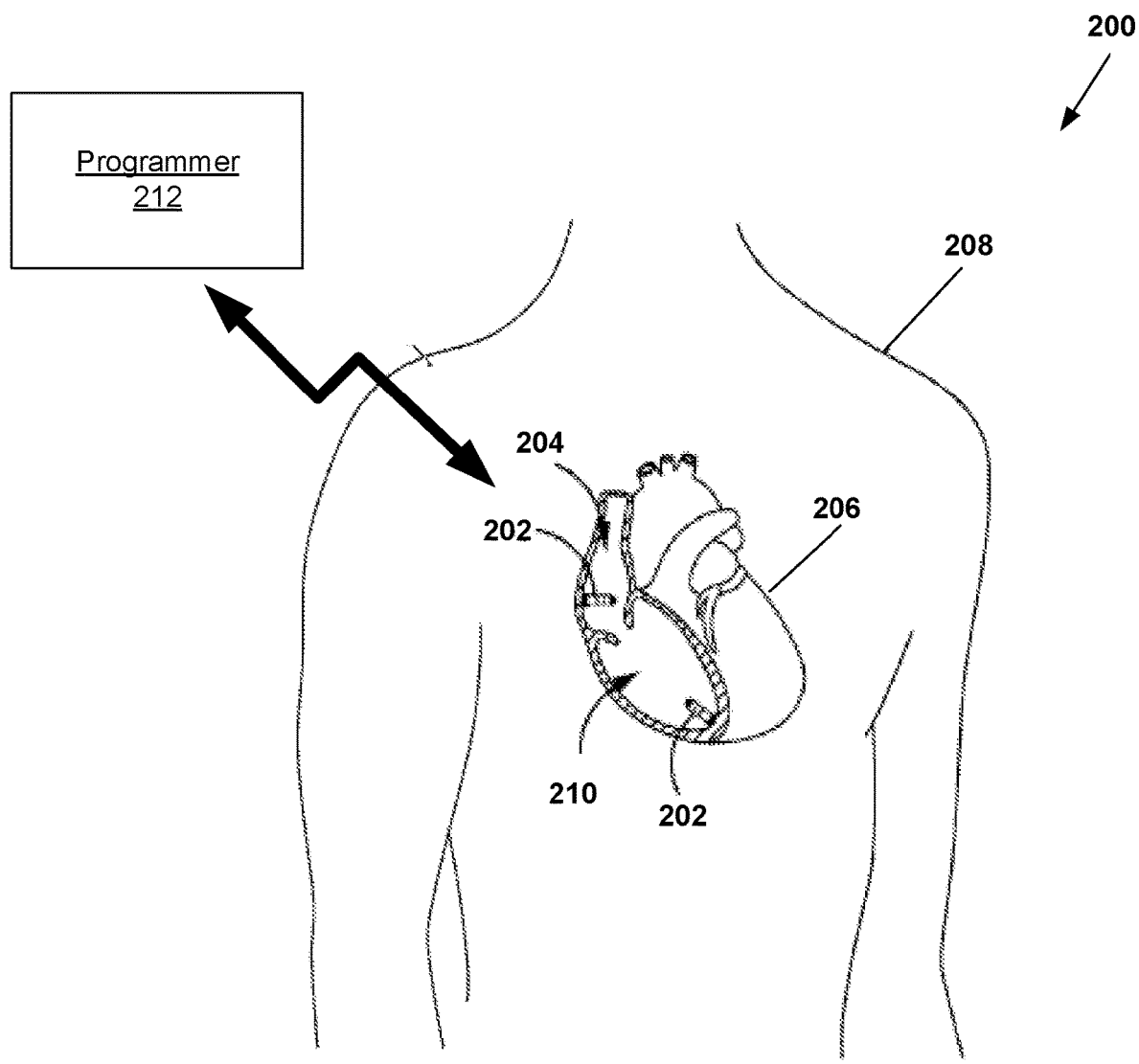
FIG. 1 is a schematic diagram illustrating a cardiac pacing device for delivering a pacing therapy according to an example of the present disclosure.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-9. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary system, device and methods described herein involve determining relevant timing parameters reflecting different intervals of mechanical events that occur during the cardiac cycle and that are sensed by an activity sensor, such as an accelerometer, located within a leadless pacing device. In one example, the leadless pacing device may be positioned within one or more chambers of a patient's heart, such as within the left ventricle of the patient, for example. The timing parameters may be determined when the pacing device determines that both the heart rate and heart rhythm are regular and are not associated with the occurrence of a tachycardia event, such as when the heart rate is less than 100 beats-per-minute (bpm), for example.

Based upon the occurrence of either a sensed ventricular event or a paced ventricular event, or sensed ventricular beat, the pacing device may determine a window of an accelerometer signal that extends, relative to the ventricular event for a period of time, such as approximately 260 ms for example. A first peak of a rectified slope of the accelerometer signal (|d(accelerometer)/dt|) within the window is determined, and the timing of the first peak of the rectified slope corresponds to a surrogate of the time indicative of early systole, i.e., early contraction of the ventricle. A second peak of the accelerometer signal is also determined within a window that begins 200 ms after the ventricular event and ends 600 ms after the ventricular event. The second peak serves as a fiducial indicative of the end of systole.

The time period extending from the ventricular event to the first peak is identified as a surrogate measurement of a pre-ejection period (PEP) for the corresponding cardiac cycle, which is typically longer for failing/asynchronous heart function. The time period extending from the first peak to the second peak is identified as a surrogate measurement of an LV ejection time (LVET) for the corresponding cardiac cycle, which is typically longer during normal synchronized pump function and shorter for failing hearts. A ratio r=PEP/LVET may be determined as an indicator of overall cardiac function, with a PEP/LVET having a greater value being associated with higher dyssynchrony and reduced efficiency in the pumping of the heart.

In one example, the pacing device may periodically or continuously monitor these data on a cycle by cycle basis and generate a trend plot over time showing how the three parameters, PEP. LVET and PEP/LVET vary. In another example, worsening heart failure may be determined to be occurring if two or more of the following occur:
 i) PEP increases by a certain threshold over the last five days, such as a greater than 20% increase, for example, or increases above a predetermined threshold value, such as 400 ms for example.
 ii) LVET decreases by a certain threshold over the last five days, such as a greater than 20% decrease, for example, or decreases below a predetermined threshold value, such as 150 ms for example.
 iii) the ratio r of the PEP to the LVET, r=PEP/LVET, increases by a predetermined threshold over the last five days, such as an average increase greater than 20% for example, or increases above a predetermined threshold value, such as 0.5 for example.

In one example, once worsening heart failure is determined, an alert may be generated by the pacing device. In another example, the pacing device may adjust pacing parameters, such as an AV delay, or a pacing rate for example, resulting in improved synchronization if markers of dyssynchrony, such as PEP increasing or the ratio of PEP/LVET increasing. In another example the pacing device may continue to auto-tune AV delays (i.e., either decreasing or increasing the AV-delay) on a cycle-by-cycle basis to bring the parameter values within certain thresholds as indicated by the markers of dyssynchrony, PEP, LVET and the ratio of PEP/LVET.

FIG. 1 is a schematic diagram illustrating a cardiac pacing device for delivering a pacing therapy according to an example of the present disclosure. As illustrated in FIG. 1, a system 200 for use in evaluation and delivery of pacing therapy according to the present disclosure may include one or more leadless pacemaker device 202 configured to be positioned within either a right atrium 204 of a heart 206 of a patient 208, within a right ventricle 210 of the patient 208, or both, as illustrated in FIG. 1. The leadless pacemaker device 202 may be configured to monitor electrical activity of the patient's 208 heart 206 and/or provide electrical therapy to the heart 206.

Figure 2:
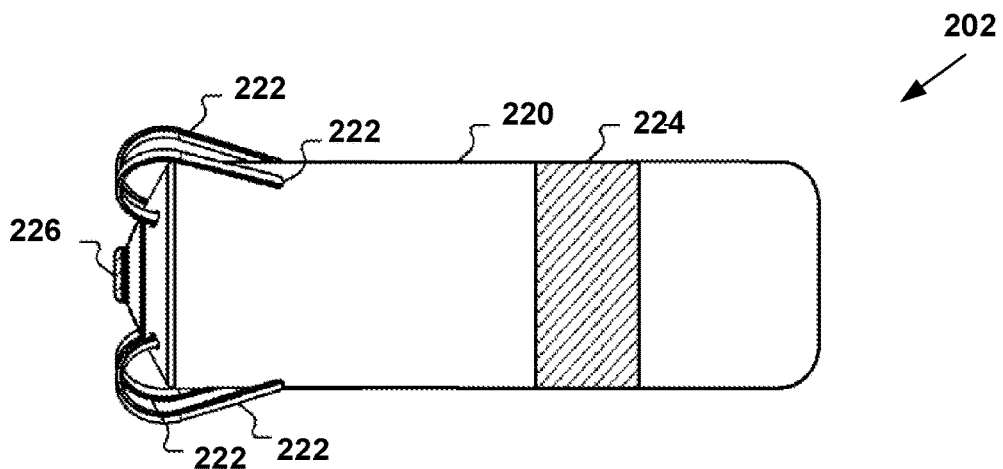
FIG. 2 is a conceptual diagram illustrating the example cardiac pacing device of FIG. 1 according to an example of the present disclosure.

FIG. 2 is a conceptual diagram illustrating the example cardiac pacing device of FIG. 1 according to an example of the present disclosure. As illustrated in FIG. 2, the leadless pacemaker device 202 includes a housing 220, fixation tines 222, a proximal electrode 224 and a distal electrode 226. The housing 220 may have a pill-shaped cylindrical form factor in some examples. The fixation tines 222 are configured to connect (e.g., anchor) device 202 to heart 206, and may be fabricated from a shape memory material, such as Nitinol. In some examples, the fixation tines 222 may connect one or both leadless pacemaker device 202 to the heart 206 within one or both of the chambers 204, 210 of the heart 206, as illustrated in FIG. 1. In another example, the fixation tines 222 may be configured to anchor a single leadless pacemaker device 202 to the heart 206 within only the right atrium 204. Although the leadless pacemaker device 202 includes a plurality of fixation tines 222 that are configured to anchor the leadless pacemaker device 202 to cardiac tissue in the right atrium 204, the left atrium 210, or both, it is contemplated that a leadless device according to the present disclosure may be fixed to cardiac tissue using other types of fixation mechanisms.

The leadless pacemaker device 202 may include one or more electrodes for sensing electrical activity of the heart 206 and/or delivering electrical stimulation to the heart 206. While the leadless pacemaker device 202 shown includes two electrodes 224, 226, more than two electrodes may be included on the leadless pacemaker device 202 in other examples. Electrode 226 may be referred to as a "tip electrode," and electrode 224 may be referred to as a "ring electrode." The fixation tines 222 may anchor the leadless pacemaker device 202 to cardiac tissue such that the tip electrode 226 maintains contact with the cardiac tissue. The ring electrode 224 may be located on the housing 220. For example, the ring electrode 224 may be a cylindrical electrode that wraps around the housing 220. Although the ring electrode 224 is illustrated as being a cylindrical electrode that wraps around the housing 220, the ring electrode 224 may include other geometries. In some examples, the housing 220 may be formed from a conductive material. In these examples, the housing 220 may act as an electrode of the leadless pacemaker device 202.

The housing 220 houses electronic components of the leadless pacemaker device 202. Electronic components may include any discrete and/or integrated electronic circuit components that implement analog and/or digital circuits capable of producing the functions attributed to the leadless pacemaker device 202 described herein. For example, the housing 220 may house electronic components that sense electrical activity via electrodes 224, 226 and/or deliver electrical stimulation via electrodes 224, 226. Additionally, the housing 220 may also include memory that includes instructions that, when executed by one or more processing circuits housed within the housing 220, cause the leadless pacemaker device 202 to perform various functions attributed to the leadless pacemaker device 202 herein. The housing 220 may also house sensors that sense physiological conditions of the patient 208, such as an accelerometer and/or a pressure sensor.

In some examples, the housing 220 may house a communication module that enables the leadless pacemaker device 202 to communicate with other electronic devices, such as a programmer 212 or other external patient monitor. In some examples, the housing 220 may house an antenna for wireless communication. The housing 220 may also include a power source, such as a battery. Electronic components included within the housing 220 are described in further detail hereinafter.

Figure 3:
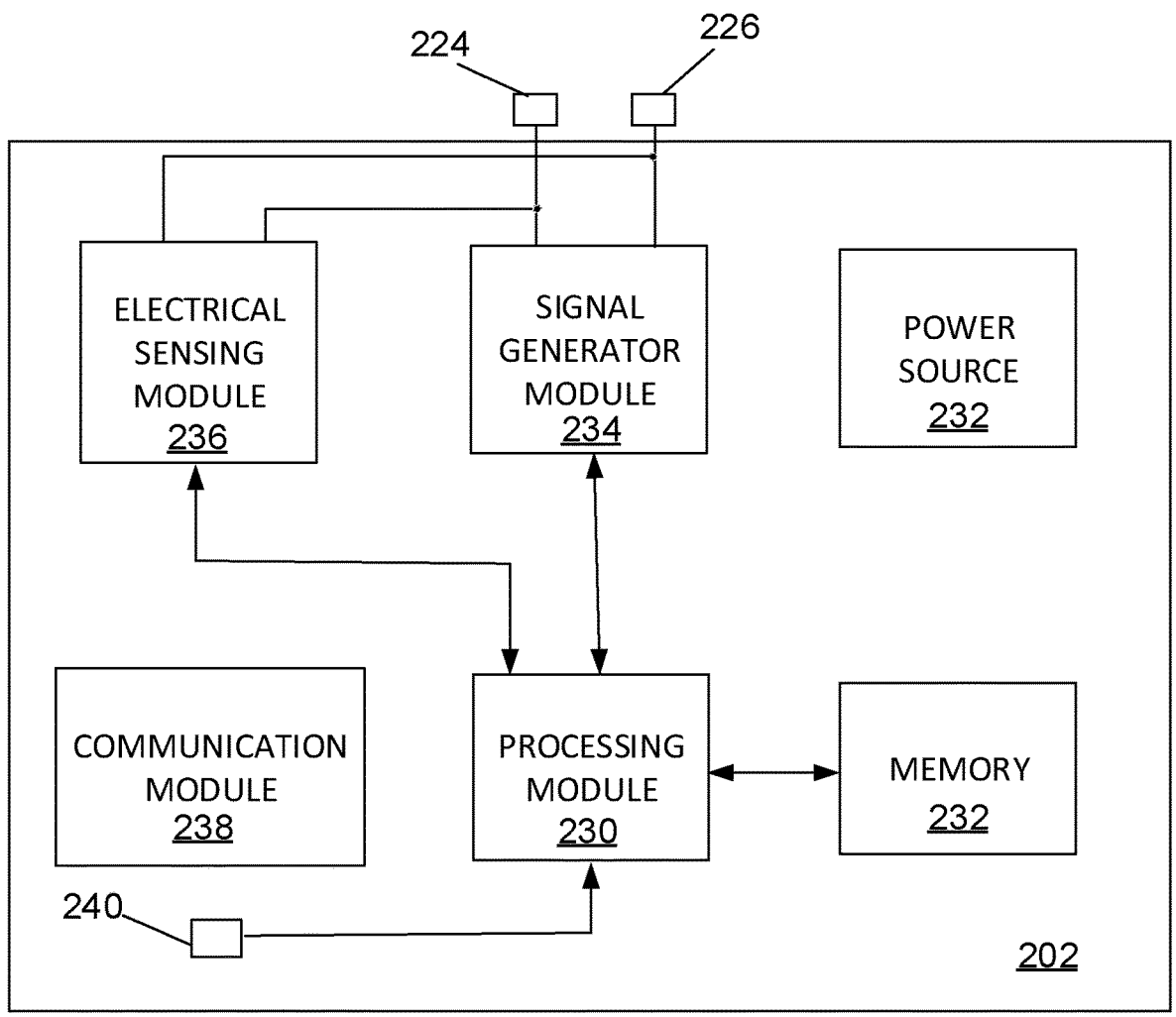
FIG. 3 is a functional block diagram of an example leadless cardiac pacemaker device according to an example of the present disclosure.

FIG. 3 is a functional block diagram of an example leadless cardiac pacemaker device according to an example of the present disclosure. FIG. 3 shows a system including a leadless pacemaker device 202 positioned in the atrium 204 of the heart 206, a leadless pacemaker device 202 positioned within the ventricle 210 of the heart 206, and a programmer 212 that may be used to program one or both leadless pacemaker device 202 and/or to retrieve data from one or both leadless pacemaker device 202. Each leadless pacemaker device 202 may include a processor or processing module 230, memory 232 a signal generator module 234, an electrical sensing module 236, a communication module 238, a sensor 240, and a power source 242. The power source 242 may include a battery, e.g., a rechargeable or non-rechargeable battery.

The modules included in the leadless pacemaker device 202 represent functionality that may be included in each of the leadless pacemaker devices 202, and may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

The processing module 230 may communicate with the memory 232. The memory 232 may include computer-readable instructions that, when executed by the processing module 230, cause the processing module 230 to perform the various functions attributed to the processing module 230 herein. The memory 232 may include any volatile, non-volatile, magnetic, or electrical media, such as RAM, ROM, NVRAM, EEPROM, Flash memory, or any other digital media. For example, the memory 232 may include pacing instructions and values, such as the baseline atrial pacing rate, the baseline atrial pacing interval and the baseline AV interval. The pacing instructions and values may be updated by the programmer 212 (FIG. 1). Pacing instructions included in the memory 232 may cause the leadless pacemaker device 202 to operate as described herein.

The processing module 230 may communicate with the signal generator module 234 and the electrical sensing module 236. The signal generator module 234 and the electrical sensing module 236 are electrically coupled to the electrodes 224, 226. The electrical sensing module 236 is configured to monitor signals from the electrodes 224, 226 in order to monitor electrical activity of the heart 206. The signal generator module 234 is configured to deliver electrical stimulation to one or both of the atrium 204 of the heart 206 and the ventricle 210 of the heart 206 via the electrodes 224, 226.

The processing module 230 may control signal the signal generator module 234 to generate and deliver electrical stimulation to one or both of the atrium 204 of the heart 206 and the ventricle 210 of the heart 206 via the electrodes 224, 226. Electrical stimulation may include pacing pulses. In some examples, electrical stimulation may also include anti-tachycardia pacing (ATP) therapy. The processing module 230 may control the signal generator module 234 to deliver electrical stimulation therapy according to one or more atrial or ventricular therapy programs including pacing instructions and values, which may be stored in the memory 232.

The electrical sensing module 236 may include circuits that acquire electrical signals. Electrical signals acquired by the electrical sensing module 236 may include intrinsic cardiac electrical activity, such as intrinsic atrial and/or intrinsic ventricular cardiac electrical activity. The electrical sensing module 236 may filter, amplify, and digitize the acquired electrical signals to generate raw digital data. The processing module 230 may receive the digitized data generated by the electrical sensing module 236. In some examples, the processing module 230 may perform various digital signal processing operations on the raw data, such as digital filtering.

The processing module 230 may sense cardiac events based on the data received from the electrical sensing module 236. For example, the processing module 230 may sense atrial events based on the data received from the electrical sensing module 236. In some examples, the processing module 230 may sense ventricular activation based on the data received from the electrical sensing module 236. For example, the processing module 230 may detect FFRWs indicative of ventricular activation based on the data received from the electrical sensing module 236.

The sensor 240 may comprise at least one of a variety of different sensors. For example, the sensor 240 may comprise at least one of a pressure sensor, a heart sounds sensor, and an accelerometer. The sensor 240 may generate signals that indicate at least one of an activity level of the patient 208, a hemodynamic pressure, and heart sounds. The processing module 230 may detect, for example, an activity level of the patient 208 based on a sensed accelerometer signal, a hemodynamic pressure signal, and a heart sounds signal based on the signals generated by the sensor 240.

The communication module 238 may include any suitable hardware (e.g., an antenna), firmware, software, or any combination thereof for communicating with another device, such as the programmer 212 or a patient monitor. Under the control of the processing module 230, the communication module 238 may receive downlink telemetry from and send uplink telemetry to other devices, such as the programmer 212 (FIG. 1) or a patient monitor, with the aid of an antenna included in the communication module 238. As described herein, a leadless pacing system may coordinate pacing of the heart 206 based on sensed cardiac electrical and/or mechanical activity without establishment of a communication link between the leadless pacemaker devices 202. Accordingly, the communication module 238 is not required to include functionality that provides for communication between the leadless pacemaker devices 202.

The programmer 212 may be a handheld computing device, desktop computing device, a networked computing device, etc. The programmer 212 may include a computer-readable storage medium having instructions that cause a processor of the programmer 212 to provide the functions attributed to the programmer 212 in the present disclosure. One or both of the leadless pacemaker devices 202 may wirelessly communicate with the programmer 212. For example, the leadless pacemaker devices 202 may transfer data to the programmer 212 and may receive data from the programmer 212. The programmer 212 may also wirelessly program and/or wirelessly charge the leadless pacemaker devices 202.

Data retrieved from the leadless pacemaker devices 202 using the programmer 212 may include cardiac EGMs stored by the leadless pacemaker devices 202 that indicate electrical activity of the heart 206 and marker channel data that indicates the occurrence and timing of sensing, diagnosis, and therapy events associated with the leadless pacemaker devices 202. Data transferred to the leadless pacemaker devices 202 using the programmer 212 may include, for example, operational programs and/or settings for the leadless pacemaker devices 202 that cause the leadless pacemaker devices 202 to operate as described herein.

The processing module 230 may control atrial pacing timing based on the detection of ventricular activation events in a variety of different ways. The manner in which the processing module 230 controls atrial pacing timing may depend on when a ventricular activation event occurs relative to the atrial event that preceded the ventricular activation event. In other words, the manner in which the processing module 230 controls atrial pacing timing may depend on when processing module detects a FFRW or an S1 heart sound relative to the atrial event that preceded the detected FFRW or the detected S1 heart sound.

Figure 4:
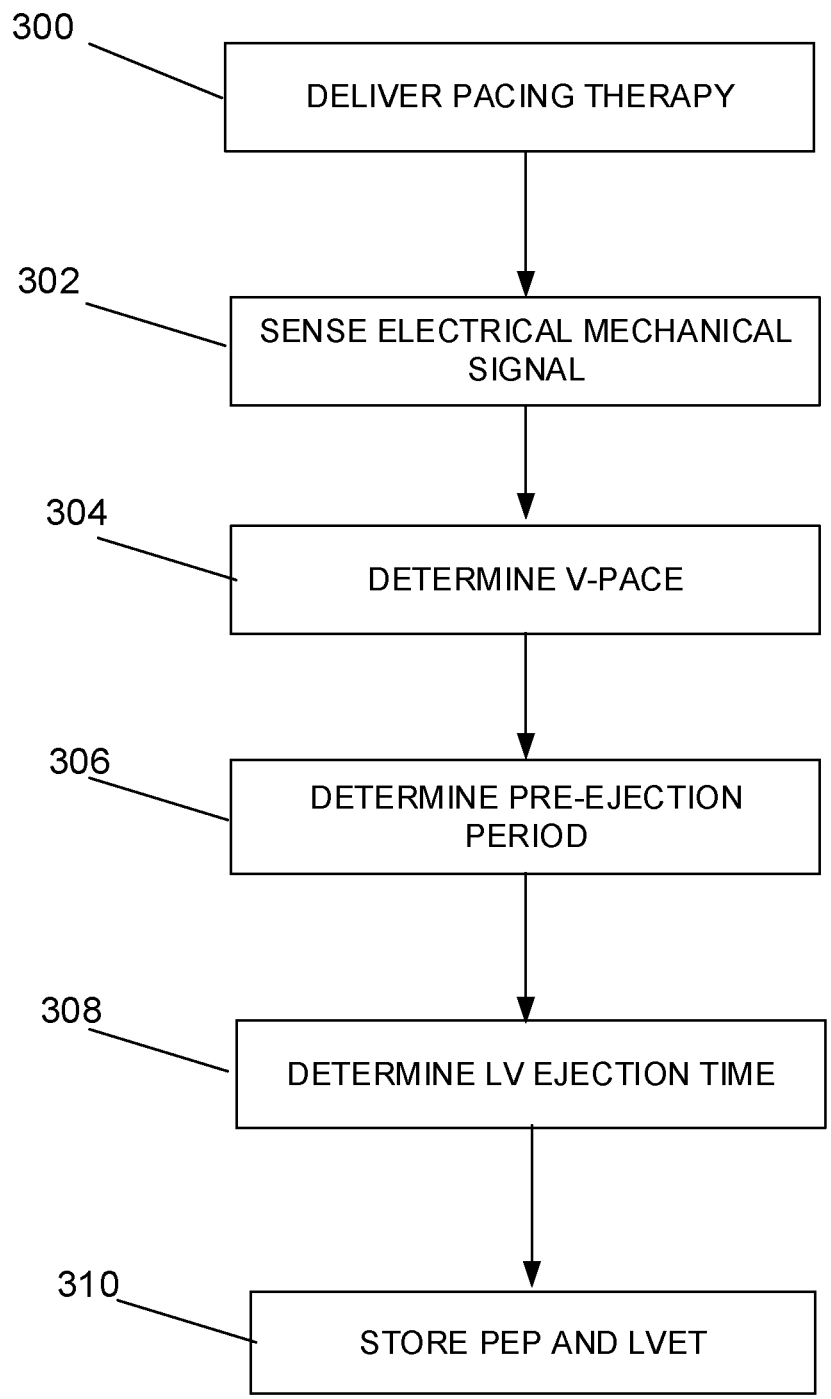
FIG. 4 is a flowchart of a method of delivering a cardiac pacing therapy according to an example of the present disclosure.

FIG. 4 is a flowchart of a method of delivering a cardiac pacing therapy according to an example of the present disclosure. As illustrated in FIG. 4, a method of delivering a cardiac pacing therapy according to an example of the present disclosure may include initially delivering a pacing therapy via electrodes 224, 226 of the pacing device 202, Block 300, during a time when processing module 230 of the pacing device 202 determines that the current rate and rhythm of the patient's heart is regular and not presently exhibiting atrial or ventricular tachyarrhythmia, such as when the current heart rate is less than 100 bpm for example. During delivery of the initial pacing therapy, the pacing device 202 senses a far-field cardiac signal via electrodes 224, 226 and an electromechanical signal, Block 302, such as an accelerometer signal sensed via sensor 240. The processing module 230 determines, based on the sensed far-field signal, when a ventricular paced (V-Pace) beat occurs, Block 304. Once a V-pace beat is determined to occur, the processing module 230 determines one or more markers of cardiac mechanical function from the sensed electromechanical signal. For example, the processing module 230 may determine a pre-ejection period (PEP) associated with the current delivered V-pace beat, Block 306, and a left ventricular ejection time (LVET) associated with the current delivered V-pace beat, Block 308. The determined initial PEP and initial LVET are then stored in the memory 232 of the pacing device 202, Block 310.

Figure 5:
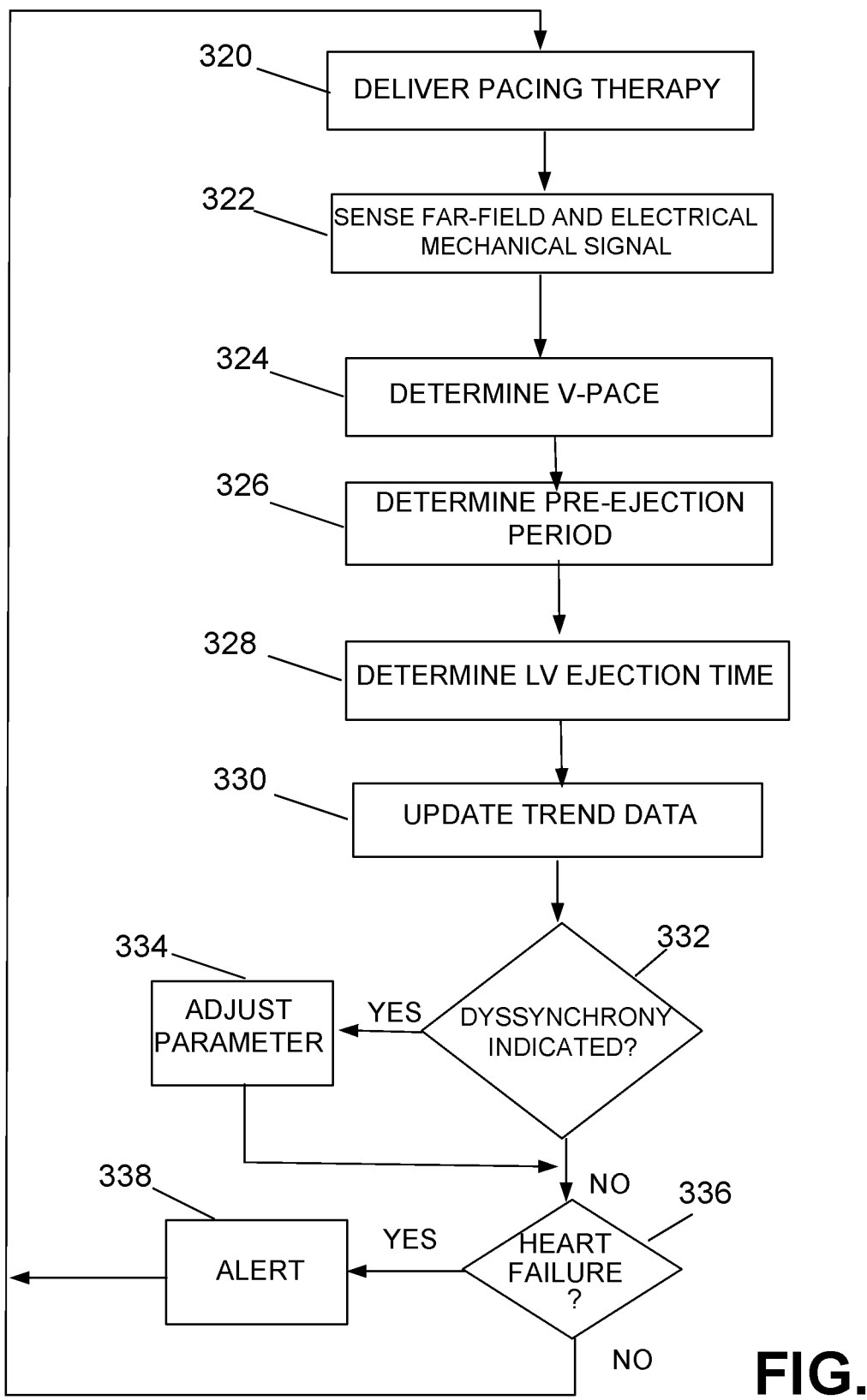
FIG. 5 is a flowchart of a method of delivering a cardiac pacing therapy according to an example of the present disclosure.

FIG. 5 is a flowchart of a method of delivering a cardiac pacing therapy according to an example of the present disclosure. As illustrated in FIG. 5, once the processing module 230 determines the initial markers of cardiac electromechanical function, PEP and LVET, during a time when processing module 230 of the pacing device 202 determines that the current rate and rhythm of the patient's heart is regular and not presently exhibiting atrial or ventricular tachyarrhythmia, the pacing device 202 subsequently delivers a pacing therapy using initial pacing parameters associated with the pacing therapy delivered during the initial determination of the markers, such as an initial pacing rate and an initial AV interval, Block 320.

During subsequent delivery of the pacing therapy, the pacing device 202 senses a far-field cardiac signal via electrodes 224, 226 and an electromechanical signal, Block 322, such as an accelerometer signal sensed from sensor 240. The processing module 230 determines, based on the far-field signal, when a pacing event, such as a ventricular paced (V-Pace) beat occurs, Block 324. Once a V-pace beat is determined to occur, the processing module 230 determines a pre-ejection period (PEP) associated with the current sensed V-pace beat, Block 326, a left ventricular ejection time (LVET) associated with the current sensed V-pace beat, Block 328, and updates trends based on the current determined PEP and LVET, Block 330. The processing module 230 then determines, based on the current PEP and LVET, whether dyssynchrony is occurring, Block 332. If dyssynchrony is determined to be occurring, Yes in Block 332, the processing module 230 adjusts one or more of the pacing parameters of the pacing therapy, Block 334, such as an AV-delay or a pacing rate, for example.

In addition to determining whether dyssynchrony is indicated or determined to occur, Block 332, the processing module 230 may also determine whether worsening heart failure is being indicated based on the current PEP and LVET, Block 336. If worsening heart failure is indicated, Yes in Block 336, an alert may be generated by the processing module 230, Block 338, and the process is repeated for the next beat, Block 320, using the adjusted parameter setting, Block 334, that was adjusted if dyssynchrony was determined to be occurring for the current beat, Yes in Block 332, and using the current, non-adjusted parameter settings if dyssynchrony was not determined to be occurring for the current beat, No in Block 332. On the other hand, if worsening heart failure is not indicated, No in Block 336, an alarm is not generated and the process is repeated for the next beat, Block 320, using the adjusted parameter setting, Block 334, that was adjusted if dyssynchrony was determined to be occurring for the current beat, Yes in Block 332, and using the current, non-adjusted parameter settings if dyssynchrony was not determined to be occurring for the current beat, No in Block 332.

While both the determination of dyssynchrony, Block 332 and the determination of worsening heart failure, Block 336, are included in the FIG. 5, it is understood, that, in one example, during monitoring of the markers of cardiac mechanical function, i.e., PEP and LVET, the processing module 230 may periodically or continuously generate a trend plot over time indicative of the variation in the markers over time, and only perform the alerting of the patient or a clinician when worsening heart failure is determined to occur. In another example, the processing module 230 may only periodically or continuously adjust one or more settings of pacing parameters, such as AV-delay or pacing rate, to deliver improved resynchronization if the markers indicate dyssynchrony so as to bring the values of the pacing parameters within certain desired thresholds. In another example, the processing module 230 may perform both the generation of the alert if worsening heart failure is indicated and the adjusting of the one or more pacing parameters of the delivered pacing therapy if dyssynchrony is determined to occur based on the trend data.

Figure 6:
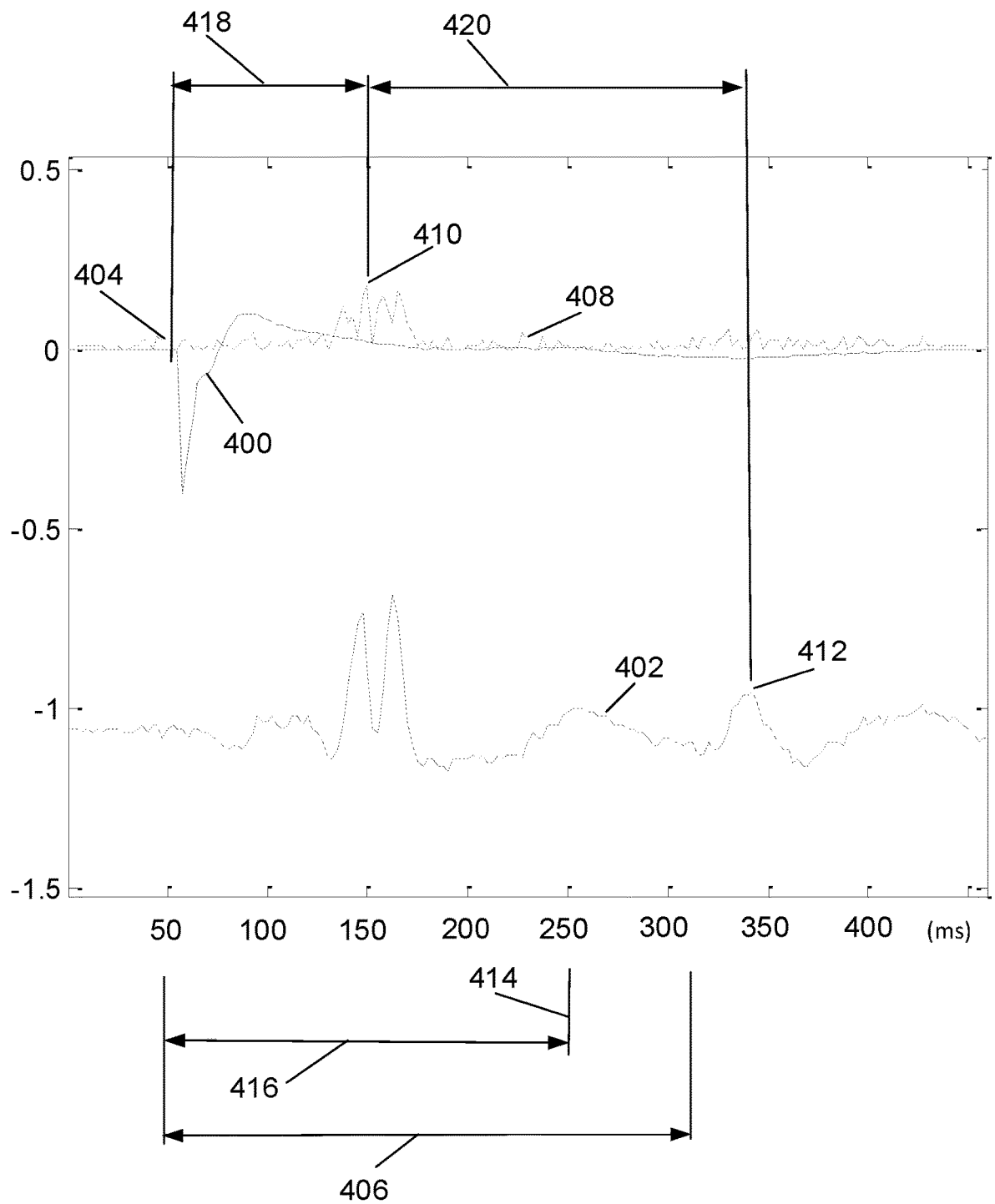
FIG. 6 is a graphical representation of determining markers of cardiac electromechanical function during delivery of a pacing therapy by a leadless cardiac pacing device, according to an example of the present disclosure.

FIG. 6 is a graphical representation of determining markers of cardiac electromechanical function during delivery of a pacing therapy by a leadless cardiac pacing device, according to an example of the present disclosure. As illustrated in FIG. 6, during delivery of the initial pacing therapy via electrodes 224, 226 the processing module 230 of the pacing device 202 determines a near-field signal 400 sensed by sensing electrodes of the pacing device, and an EM signal 402 sensed by an EM sensor of the pacing device. The processing module 230 identifies timing of the occurrence of a ventricular pace (VP) event 404 from the near-field signal 400 and determines a time window 406 extending a predetermined time period from the sensed VP event 404. In one example, the predetermined time period of time window 406 may be approximately 260 ms.

In addition, the processing module 230 determines a rectified derivative signal 408 of the EM signal 402 and determines timing indicative of the occurrence of early systole by determining a maximum 410 of the rectified derivative signal 408 that occurs within the time window 406. In addition, the processing module 230 determines timing indicative of the occurrence of the end of systole by determining a maximum 412 of the accelerometer signal 402 that occurs during a second time window having a start point 414 located a predetermined distance 416 from the sensed V-pace event 404 and that extends a predetermined time period from the start point 414. In one example, the start point 414 may be located 200 ms from the V-pace event 404 and the second time window may extend a predetermined time period of 600 ms from the start point 414 of the second time window.

In this way, during initial delivery of pacing therapy determines one or more marker of cardiac mechanical function from the sensed electromechanical signal. For example, once the V-pace event 404 is identified, and the maximum 410 of the rectified derivative signal 408 and the maximum 412 of the accelerometer signal 402 are determined relative to the V-pace event 404, the processing module 230 may determine a pre-ejection period (PEP) 418 extending between the V-pace event 404 and the maximum 410 of the rectified derivative signal 408, and a left ventricular ejection time (LVET) 420 extending from the maximum 410 of the rectified derivative signal 408 to the maximum 412 of the accelerometer signal 402. The determined initial pre-ejection period (PEP) 418 and initial left ventricular ejection time (LVET) 420 are then stored in the memory 232 of the pacing device 202.

Figure 7:
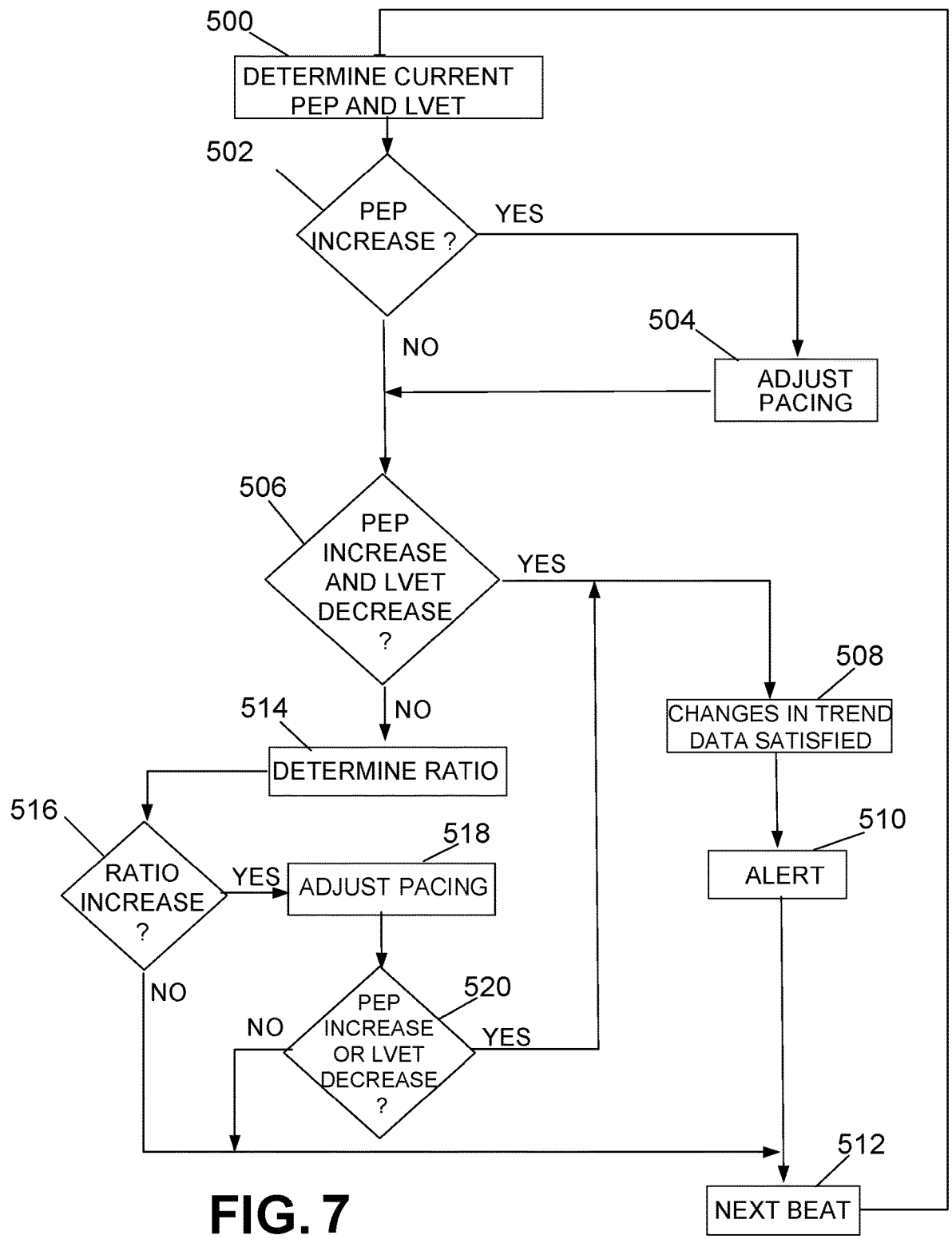
FIG. 7 is a flow chart of a method of delivering a cardiac pacing therapy according to an example of the present disclosure.

FIG. 7 is a flow chart of a method of delivering a cardiac pacing therapy according to an example of the present disclosure. As described above, in one example, during monitoring of the markers of cardiac mechanical function, i.e., PEP and LVET, the processing module 230 may periodically or continuously generate a trend plot over time indicative of the variation in the markers over time, and only perform the generation of the alert if worsening heart failure is determined to be occurring. In another example, the processing module 230 may only periodically or continuously adjust one or more settings of pacing parameters, such as AV-delay or pacing rate, by either increasing or decreasing the parameter setting to deliver improved resynchronization if the markers indicate dyssynchrony, so as to bring the values of the pacing parameters within certain desired thresholds. In another example, the processing module 230 may perform both the generating of the alert of worsening heart failure and the adjusting of the one or more pacing parameters of the delivered pacing therapy based on the updated trend data.

For example, as illustrated in FIGS. 6 and 7, once the initial pre-ejection period (PEP) 418 and initial left ventricular ejection time (LVET) 420 have been determined and stored, described above, the pacing device 202 subsequently delivers a pacing therapy having the initial pacing parameters settings associated with the pacing therapy delivered by the pacing device 202 during the determination of the initial pre-ejection period (PEP) 418 and initial left ventricular ejection time (LVET) 420, described above. The processing module 230 of the pacing 202 determines, on a beat-by-beat basis, the pre-ejection period (PEP) 418 and initial left ventricular ejection time (LVET) 420 associated with each subsequently sensed V-pace event 404, Block 500, and stores the determined current pre-ejection period (PEP) 418 and initial left ventricular ejection time (LVET) 420 for each sensed V-pace event 404. The processing module 230 then updates trend data over time using the current determined PEP 418 and LVET 420 in such a way as to be indicative of how the PEP 418 and LVET 420 have varied over time.

Based on the updated trended data, including the current pre-ejection period (PEP) 418 and initial left ventricular ejection time (LVET) 420 data, the processing module 230 determines whether there is a predetermined increase in the PEP 418, such as a greater than 20 percent increase on average, over a predetermined number of days, such as 5 days, for example, Block 502. If there is an increase in the PEP 418, Yes in Block 502, indicating dyssynchrony, the pacing device may adjust one or more pacing parameters of the pacing therapy, Block 504, such as the AV-delay or pacing rate, for example. In addition, the processing module 230 determines whether there is both an increase in the current PEP 418 and a decrease in the current determined LVET 420 over a predetermined number of days, such as 5 days for example, Block 506. If there is both an increase in the current PEP 418 and a decrease in the current determined LVET 420, Yes in Block 506, changes in trend data are determined to be satisfied, Block 508, and therefore worsening heart failure is indicated.

In response to the indication of worsening heart failure, an alert may be generated, and the process is repeated for the next beat, Block 512, using the adjusted parameter setting, Block 504, that was adjusted if the predetermined increase in the PEP 418 was determined to occur for the current sensed V-pace beat 404, Yes in Block 502. On the other hand, the process is repeated for the next beat Block 512 using the current, non-adjusted parameter settings if the predetermined increase in the PEP 418 was not determined to occur for the current sensed V-pace beat 404, No in Block 502.

If there is not both an increase in the current PEP 418 and a decrease in the current determined LVET 420, No in Block 506, the processing module 230 determines a ratio of the PEP 418 and the LVET 420, Block 514, updates the ratio of the determined PEP 418 and the LVET 420 over multiple sensed V-pace events, and determines whether there is an increase in the ratio of the PEP 418 and the LVET 420, Block 516, indicative of dyssynchrony. In one example, an increase in the ratio of PEP to LVET indicative of dyssynchrony may be determined to occur if the ratio increases by a predetermined threshold over a predetermined number of days. For example, an increase in the ratio may be determined to occur if the ratio increases by more than 20 percent over five days. In another example, an increase in the ratio may be determined to occur if the ratio is greater than a predetermined threshold, such as 0.5, for example.

If an increase in the ratio of the PEP 418 and the LVET 420 is not determined to occur, No in Block 516, the process is repeated for the next beat, Block 512, using the adjusted parameter setting, Block 504, that was adjusted if the predetermined increase in the PEP 418 was determined to occur for the current sensed V-pace beat 404, Yes in Block 502. On the other hand, the process is repeated for the next beat Block 512 using the current, non-adjusted parameter settings if the predetermined increase in the PEP 418 was not determined to occur for the current sensed V-pace beat 404, No in Block 502.

If an increase in the ratio of the PEP 418 and the LVET 420 is determined to occur, Yes in Block 516, the processing module 230 may adjust one or more pacing parameters of the pacing therapy, Block 518, such as the AV-delay or pacing rate, for example, and a determination is made as to whether there is either an increase in the PEP 418 or a decrease in the LVET 420, Block 520. If there is not one of an increase in the PEP 418 or a decrease in the LVET 420, No in Block 520, heart failure is not indicated and the process is repeated for the next beat, Block 512, using the current, non-adjusted parameter settings, i.e., without any parameter adjustment having been made for the current sensed V-pace event 404.

If there is either an increase in the PEP 418 or a decrease in the LVET 420, Yes in Block 520, changes in trend data are determined to be satisfied, Block 508, and therefore worsening heart failure is indicated. In response to the indication of worsening heart failure, an alert may be generated, and the process is repeated for the next beat, Block 512, using the adjusted parameter setting, Block 504, that was adjusted if the predetermined increase in the PEP 418 was determined to occur for the current sensed V-pace beat 404, Yes in Block 502. On the other hand, the process is repeated for the next beat Block 512 using the current, non-adjusted parameter settings if the predetermined increase in the PEP 418 was not determined to occur for the current sensed V-pace beat 404, No in Block 502.

In this way, based upon the occurrence of either a sensed ventricular event or a paced ventricular event, or sensed ventricular beat, the pacing device may determine a window of an accelerometer signal that extends, relative to the ventricular event for a period of time, such as approximately 260 ms for example. A first peak of a rectified slope of the accelerometer signal (|d(accelerometer)/dt) within the window is determined, and the timing of the first peak of the rectified slope corresponds to a surrogate of the time indicative of early systole, i.e., early contraction of the ventricle. A second peak of the accelerometer signal is also determined within a window that begins 200 ms after the ventricular event and ends 600 ms after the ventricular event. The second peak serves as a fiducial indicative of the end of systole.

The time period extending from the ventricular event to the first peak is identified as a surrogate measurement of a pre-ejection period (PEP) for the corresponding cardiac cycle, which is typically longer for failing/asynchronous heart function. The time period extending from the first peak to the second peak is identified as a surrogate measurement of an LV ejection time (LVET) for the corresponding cardiac cycle, which is typically longer during normal synchronized pump function and shorter for failing hearts. A ratio r=PEP/LVET, which serves as an indicator of overall cardiac function, i.e., a greater ratio value being associated with increased dyssynchrony and reduced efficiency, may be determined as an indicator of overall cardiac function, with a PEP/LVET having a greater value being associated with higher dyssynchrony and reduced efficiency in the pumping of the heart.

In one example, the pacing device may periodically or continuously monitor these data on a cycle by cycle basis and generate a trend plot over time showing how the three parameters, PEP, LVET and PEP/LVET vary. In another example, worsening heart failure may be determined to be occurring if two or more of the following occur:

i) PEP increases by a certain threshold over the last five days, such as a greater than 20% increase, for example, or increases above a predetermined threshold value, such as 400 ms for example.
  ii) LVET decreases by a certain threshold over the last five days, such as a greater than 20% decrease, for example, or decreases below a predetermined threshold value, such as 150 ms for example.
  iii) the ratio r=PEP/LVET increases by a predetermined threshold over the last five days, such as an average increase greater than 20% for example, or increases above a predetermined threshold value, such as 0.5 for example.

In one example, once worsening heart failure is determined, an alert may be generated by the pacing device. In another example, the processing module 230 may adjust pacing parameters, such as an AV delay, or a pacing rate for example, resulting in improved synchronization of markers of dyssynchrony, if either the PEP 418 is determined to be increasing or the ratio of PEP/LVET is determined to be increasing. In this way, the pacing device 202 may continue to auto-tune AV delays (i.e., either decreasing or increasing the AV-delay) on a cycle-by-cycle basis to bring the parameter values within certain thresholds as indicated by the markers of dyssynchrony, PEP, LVET and the ratio of PEP/LVET.

Figure 8:
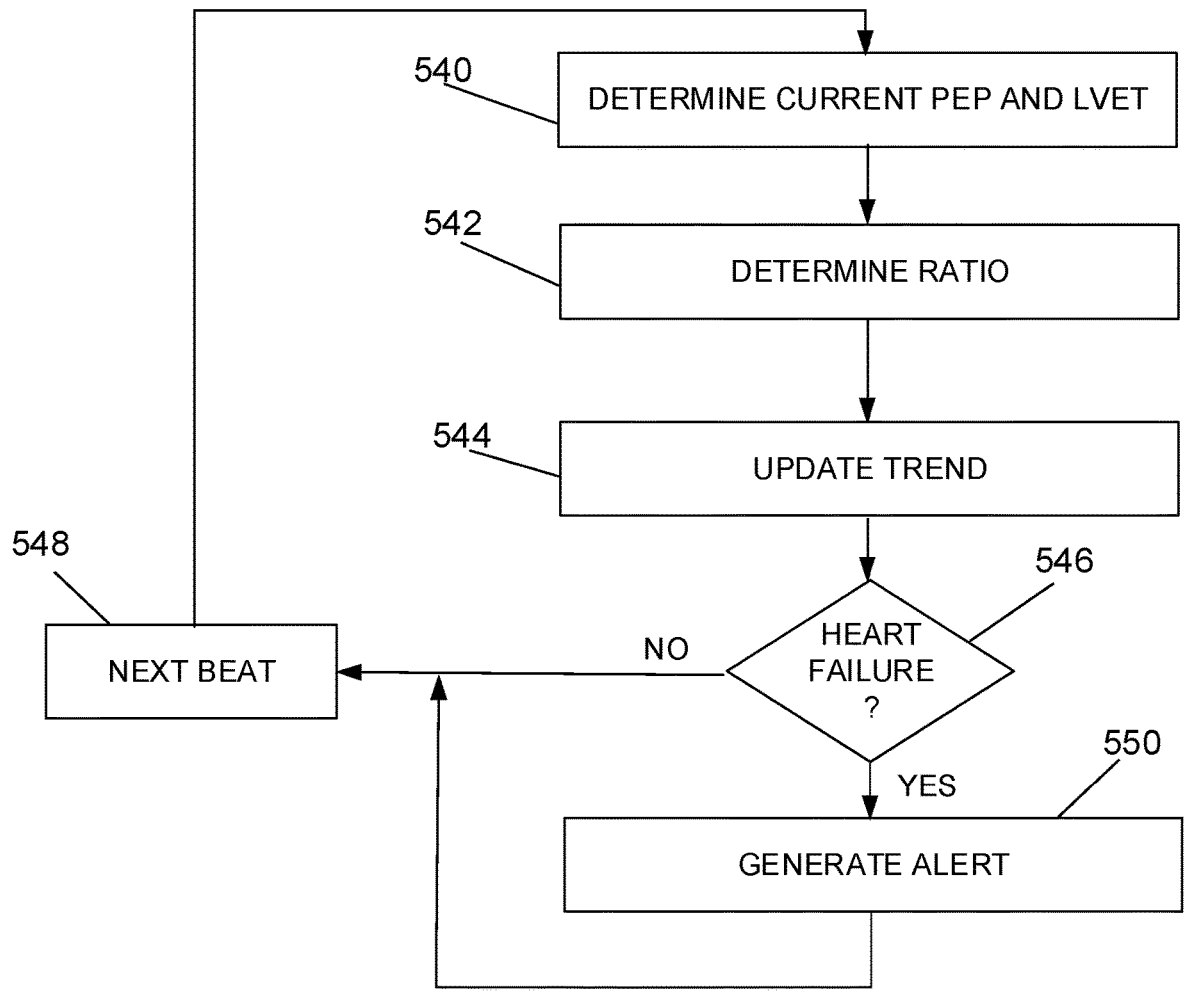
FIG. 8 is a flow chart of a method of delivering a cardiac pacing therapy according to an example of the present disclosure.

FIG. 8 is a flow chart of a method of delivering a cardiac pacing therapy according to an example of the present disclosure. While in the example method of delivering a cardiac pacing therapy described in FIG. 7 includes both adjusting pacing parameters when dyssynchrony is determined to occur and generating an alarm when worsening heart failure is determined, it is understood, that, in one example, the processing module 230 may periodically or continuously generate a trend plot over time indicative of the variation in the markers of cardiac mechanical function, i.e., PEP and LVET, over time, and perform only the generation of the alert if worsening heart failure determined to be occurring. For example, as illustrated in FIGS. 6 and 8, once the initial pre-ejection period (PEP) 418 and initial left ventricular ejection time (LVET) 420 have been determined and stored, described above, the pacing device 202 subsequently delivers a pacing therapy having the initial pacing parameters settings associated with the pacing therapy delivered by the pacing device 202 during the determination of the initial pre-ejection period (PEP) 418 and initial left ventricular ejection time (LVET) 420, described above. The processing module 230 determines, on a beat-by-beat basis, the pre-ejection period (PEP) 418, the left ventricular ejection time (LVET) 420, Block 540, and the ratio of the PEP 412 and LVET 420, Block 542, associated with each subsequently sensed V-pace event 404, and updates trend data, Block 544, using the current determined PEP 418 and LVET 420 in such a way as to be indicative of how the PEP 418, the LVET 420 and a ratio of the PEP and LVET have varied over time.

Based on the updated trended data, Block 544, including the current pre-ejection period (PEP) 418 and initial left ventricular ejection time (LVET) 420 data, the processing module 230 determines whether the pre-ejection period (PEP) 418 is increasing, whether the left ventricular ejection time (LVET) 420 is decreasing, and whether the ratio of the PEP 418 and the LVET 420 is increasing over multiple sensed V-pace events, Block 544. The processing module 230 determines whether heart failure is occurring, Block 546, based on whether at least two of an increase in the PEP, a decrease in the LVET and an increase in the ratio of the PEP 418 and the LVET 420 are occurring, indicative of dyssynchrony.

In one example, an increase in the ratio of PEP to LVET may be determined to occur if the ratio increases by a predetermined threshold over a predetermined number of days. For example, an increase in the ratio may be determined to occur if the ratio increases by more than 20 percent over five days. In another example, an increase in the ratio may be determined to occur if the ratio is greater than a predetermined threshold, such as 0.5, for example. An increase in PEP may be determined to be occurring if there is a predetermined increase in the PEP 418, such as a greater than 20 percent increase on average, over a predetermined number of days, such as 5 days, for example. In another example, an increase in PEP may be determined to be occurring if the PEP increases above a predetermined threshold, such as 400 ms, for example. A decrease in LVET may be determined to be occurring if there is a predetermined decrease in the current determined LVET 420, such as a greater than 20 percent decrease on average, over a predetermined number of days, such as 5 days for example. In another example, a decrease in LVET may be determined to be occurring if the LVET decreases below a predetermined threshold, such as 150 ms, for example.

If at least two of an increase in the PEP, a decrease in the LVET and an increase in the ratio of the PEP 418 and the LVET 420 are not determined to occur and therefore heart failure is not indicated, No in Block 546, the process is repeated for the next beat, Block 548. If at least two of an increase in the PEP, a decrease in the LVET and an increase in the ratio of the PEP 418 and the LVET 420 are determined to occur and therefore heart failure is indicated, Yes in Block 546, the processing module 230 may generate an alarm, Block 550, and the process is repeated for the next beat, Block 548.

In this way, worsening heart failure may be determined to be occurring if two or more of the following occur:
  i) PEP increases by a certain threshold over the last five days, such as a greater than 20% increase, for example, or increases above a predetermined threshold value, such as 400 ms for example.
  ii) LVET decreases by a certain threshold over the last five days, such as a greater than 20% decrease, for example, or decreases below a predetermined threshold value, such as 150 ms for example.
  iii) the ratio r=PEP/LVET increases by a predetermined threshold over the last five days, such as an average increase greater than 20% for example, or increases above a predetermined threshold value, such as 0.5 for example.

Figure 9:
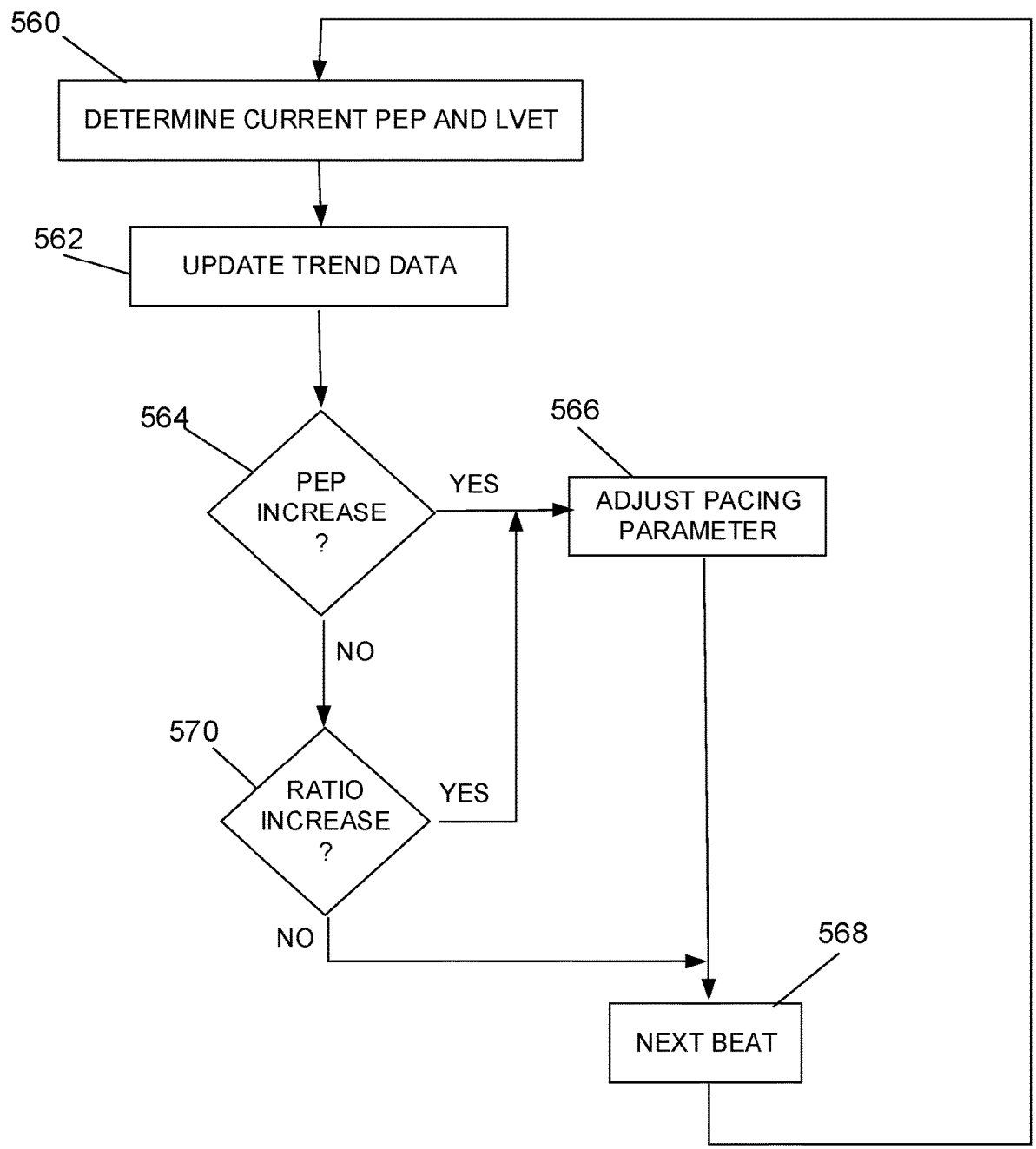
FIG. 9 is a flow chart of a method of delivering a cardiac pacing therapy according to an example of the present disclosure.

FIG. 9 is a flow chart of a method of delivering a cardiac pacing therapy according to an example of the present disclosure. As illustrated in FIGS. 6 and 9, once the initial pre-ejection period (PEP) 418 and initial left ventricular ejection time (LVET) 420 have been determined and stored, described above, the pacing device 202 subsequently delivers a pacing therapy having the initial pacing parameters settings associated with the pacing therapy delivered by the pacing device 202 during the determination of the initial pre-ejection period (PEP) 418 and initial left ventricular ejection time (LVET) 420, described above. The processing module 230 determines, on a beat-by-beat basis, the pre-ejection period (PEP) 418, the left ventricular ejection time (LVET) 420, and the ratio of the PEP 412 and LVET 420, Block 560, associated with each subsequently sensed V-pace event 404, and updates trend data, Block 562, using the current determined PEP 418 and LVET 420 in such a way as to be indicative of how the PEP 418 and a ratio of the PEP and LVET have varied over time.

Based on the updated trended data, Block 562, including the current pre-ejection period (PEP) 418 and initial left ventricular ejection time (LVET) 420 data, the processing module 230 determines, for the current sensed V-pace event 404, whether there is a predetermined increase in the PEP 418, Block 564. If there is an increase in the PEP 418, Yes in Block 564, indicating dyssynchrony, the processing module 230 may adjust one or more pacing parameters of the pacing therapy, Block 566, such as the AV-delay or pacing rate, for example, and the process is repeated for the next beat, Block 568.

If there is not an increase in the PEP 418, No in Block 564, the processing module 230 determines whether the ratio of the PEP 418 to the LVET 420 has increased, Block 570. If an increase in the ratio of the PEP 418 to the LVET 420 is not determined to occur, No in Block 570, the process is repeated for the next beat, Block 568. If an increase in the ratio of the PEP 418 to the LVET 420 is determined to occur, Yes in Block 570, indicating dyssynchrony, the processing module 230 may adjust one or more pacing parameters of the pacing therapy, Block 566, such as the AV-delay or pacing rate, for example, and the process is repeated for the next beat, Block 568. In this way, the processing module 230 may adjust pacing parameters, such as an AV delay, or a pacing rate for example, resulting in improved synchronization of markers of dyssynchrony, if either the PEP 418 is determined to be increasing, Block 564, or the ratio of PEP/LVET is determined to be increasing, Block 570. As a result, the pacing device 202 may continue to auto-tune AV delays (i.e., either decreasing or increasing the AV-delay) on a cycle-by-cycle basis to bring the parameter values within certain thresholds as indicated by the markers of dyssynchrony, PEP and the ratio of PEP/LVET.

In one example, an increase in the ratio of PEP to LVET may be determined to occur if the ratio increases by a predetermined threshold over a predetermined number of days. For example, an increase in the ratio may be determined to occur if the ratio increases by more than 20 percent over five days. In another example, an increase in the ratio may be determined to occur if the ratio is greater than a predetermined threshold, such as 0.5, for example. An increase in PEP may be determined to be occurring if there is a predetermined increase in the PEP 418, such as a greater than 20 percent increase on average, over a predetermined number of days, such as 5 days, for example. In another example, an increase in PEP may be determined to be occurring if the PEP increases above a predetermined threshold, such as 400 ms, for example.

The techniques described in this disclosure, such as those attributed to the pacing device 202, including the processing module 230, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

Illustrative Embodiments

Embodiment 1. A method of delivering a cardiac pacing therapy, comprising:
  delivering the cardiac pacing therapy from a cardiac pacing device;
  sensing a pacing event from a plurality of electrodes of the pacing device;
  sensing an electromechanical signal from an electromechanical sensor of the pacing device;
  determining a pre-ejection period in response to the sensed electromechanical signal;
  determining a left ventricular ejection time in response to the sensed electromechanical signal; and
  performing one or both of adjusting a pacing parameter setting and generating an alert in response to the determined pre-ejection period and the determined left ventricular ejection time.

Embodiment 2. The method of embodiment 1, further comprising:
  determining a maximum of a rectified derivative of the EM signal within a first time window extending a predetermined time period from the sensed pacing event; and
  determining a maximum of the EM signal within a second time window extending from a second window start point positioned a predetermined distance from the sensed pacing event, wherein the pre-ejection period is determined in response to a time period extending between the sensed pacing event and the maximum of the rectified derivative of the EM signal, and the left ventricular ejection time is determined in response to a time period extending between the second window start point and the maximum of the EM signal.

Embodiment 3. The method of any of embodiments 1 to 2, wherein the first window extends approximately 260 ms from the sensed pacing event, the second window start point is positioned approximately 200 ms from the sensed pacing event and the second window extends approximately 600 ms from the second window start point.

Embodiment 4. The method of any of embodiments 1-3, further comprising:
  determining trend data associated with the pre-ejection period, the left ventricular ejection time and a ratio of the pre-ejection period and the left ventricular ejection time for a plurality of the sensed cardiac events;
  determining whether the pre-ejection period is increasing;
  determining whether the ratio of the pre-ejection period and the left ventricular ejection time is increasing; and
  adjusting delivery of the cardiac pacing therapy in response to one of determining the pre-ejection period is increasing and determining the ratio of the pre-ejection period and the left ventricular ejection time is increasing.

Embodiment 5. The method of any of embodiments 1-4, wherein determining whether the pre-ejection period increases comprises one of determining whether the pre-ejection period increases by greater than a predetermined percentage over a predetermined number of days and determining whether the pre-ejection period increases above a predetermined numerical threshold, and wherein determining whether the ratio of the pre-ejection period increases comprises one of determining whether the ratio of the pre-ejection period and the left ventricular ejection time increases by greater than a predetermined percentage over a predetermined number of days and determining whether the ratio of the pre-ejection period and the left ventricular ejection time increases above a predetermined numerical threshold.

Embodiment 6. The method of any of embodiments 1-5, further comprising:
  determining trend data associated with the pre-ejection period, the left ventricular ejection time and a ratio of the pre-ejection period and the left ventricular ejection time for a plurality of the sensed cardiac events;
  determining whether the pre-ejection period is increasing;
  determining whether the left ventricular ejection time is decreasing;
  determining whether the ratio of the pre-ejection period and the left ventricular ejection time is increasing;
  determining whether heart failure is indicated in response to determining at least two of the pre-ejection period determined to be increasing, the left ventricular ejection time determined to be decreasing, and the ratio of the pre-ejection period and the left ventricular ejection time determined to be increasing; and
  generating an alert in response to heart failure being indicated.

Embodiment 7. The method of any of embodiments 1-6, wherein determining whether the pre-ejection period increases comprises one of determining whether the pre-ejection period increases by greater than a predetermined percentage over a predetermined number of days and determining whether the pre-ejection period increases above a predetermined numerical threshold, wherein determining whether the left ventricular ejection time decreases comprises one of determining whether the left ventricular ejection time decreases by greater than a predetermined percentage over a predetermined number of days and determining whether the left ventricular ejection time decreases above a predetermined numerical threshold, and wherein determining whether the ratio of the pre-ejection period increases comprises one of determining whether the ratio of the pre-ejection period and the left ventricular ejection time increases by greater than a predetermined percentage over a predetermined number of days and determining whether the ratio of the pre-ejection period and the left ventricular ejection time increases above a predetermined numerical threshold.

Embodiment 8. The method of any of embodiments 1-7, further comprising:
determining trend data associated with the pre-ejection period, the left ventricular ejection time and a ratio of the pre-ejection period and the left ventricular ejection time for a plurality of the sensed cardiac events;
determining whether the pre-ejection period is increasing;
determining whether the left ventricular ejection time is decreasing;
determining whether the ratio of the pre-ejection period and the left ventricular ejection time is increasing;
determining whether heart failure is indicated in response to determining at least two of the pre-ejection period determined to be increasing, the left ventricular ejection time determined to be decreasing, and the ratio of the pre-ejection period and the left ventricular ejection time determined to be increasing;
adjusting delivery of the cardiac pacing therapy in response to one of determining the pre-ejection period is increasing and determining the ratio of the pre-ejection period and the left ventricular ejection time is increasing; and
generating an alert in response to heart failure being indicated.

Embodiment 9. The method of any of embodiments 1-8, wherein determining whether the pre-ejection period increases comprises one of determining whether the pre-ejection period increases by greater than a predetermined percentage over a predetermined number of days and determining whether the pre-ejection period increases above a predetermined numerical threshold, wherein determining whether the left ventricular ejection time decreases comprises one of determining whether the left ventricular ejection time decreases by greater than a predetermined percentage over a predetermined number of days and determining whether the left ventricular ejection time decreases above a predetermined numerical threshold, and wherein determining whether the ratio of the pre-ejection period increases comprises one of determining whether the ratio of the pre-ejection period and the left ventricular ejection time increases by greater than a predetermined percentage over a predetermined number of days and determining whether the ratio of the pre-ejection period and the left ventricular ejection time increases above a predetermined numerical threshold.

Embodiment 10. The method of any of embodiments 1-9, wherein the cardiac pacing device comprises a leadless pacemaker device and the sensed pacing event comprises a ventricular pacing event.

Embodiment 11. A cardiac pacing device for delivering a cardiac pacing therapy, comprising:
one or more electrodes for sensing a cardiac event and delivering the pacing therapy;
a sensor for sensing an electromechanical signal; and
a processor configured to determine a pre-ejection period in response to the sensed electromechanical signal, determine a left ventricular ejection time in response to the sensed electromechanical signal, and perform one or both of adjusting a pacing parameter setting and generating an alert in response to the determined pre-ejection period and the determined left ventricular ejection time.

Embodiment 12. The device of embodiment 11, wherein the processor is configured to determine a maximum of a rectified derivative of the EM signal within a first time window extending a predetermined time period from the sensed pacing event, and determine a maximum of the EM signal within a second time window extending from a second window start point positioned a predetermined distance from the sensed pacing event, wherein the pre-ejection period is determined in response to a time period extending between the sensed pacing event and the maximum of the rectified derivative of the EM signal, and the left ventricular ejection time is determined in response to a time period extending between the second window start point and the maximum of the EM signal.

Embodiment 13. The device of any of embodiments 11-12, wherein the first window extends approximately 260 ms from the sensed pacing event, the second window start point is positioned approximately 200 ms from the sensed pacing event and the second window extends approximately 600 ms from the second window start point.

Embodiment 14. The device of any of embodiments 11-13, wherein the processor is configured to determine trend data associated with the pre-ejection period, the left ventricular ejection time and a ratio of the pre-ejection period and the left ventricular ejection time for a plurality of the sensed cardiac events, determine whether the pre-ejection period is increasing, determine whether the ratio of the pre-ejection period and the left ventricular ejection time is increasing, and adjust delivery of the cardiac pacing therapy in response to one of determining the pre-ejection period is increasing and determining the ratio of the pre-ejection period and the left ventricular ejection time is increasing.

Embodiment 15. The device of any of embodiments 11-14, wherein determining whether the pre-ejection period increases comprises one of determining whether the pre-ejection period increases by greater than a predetermined percentage over a predetermined number of days and determining whether the pre-ejection period increases above a predetermined numerical threshold, and wherein determining whether the ratio of the pre-ejection period increases comprises one of determining whether the ratio of the pre-ejection period and the left ventricular ejection time increases by greater than a predetermined percentage over a predetermined number of days and determining whether the ratio of the pre-ejection period and the left ventricular ejection time increases above a predetermined numerical threshold.

Embodiment 16. The device of any of embodiments 11-15, wherein the processor is configured to determine trend data associated with the pre-ejection period, the left ventricular ejection time and a ratio of the pre-ejection period and the left ventricular ejection time for a plurality of the sensed cardiac events, determine whether the pre-ejection period is increasing, determine whether the left ventricular ejection time is decreasing, determine whether the ratio of the pre-ejection period and the left ventricular ejection time is increasing, determine whether heart failure is indicated in response to determining at least two of the pre-ejection period determined to be increasing, the left ventricular ejection time determined to be decreasing, and the ratio of the pre-ejection period and the left ventricular ejection time determined to be increasing, and generate an alert in response to heart failure being indicated.

Embodiment 17. The device of any of embodiments 11-16, wherein determining whether the pre-ejection period increases comprises one of determining whether the pre-ejection period increases by greater than a predetermined percentage over a predetermined number of days and determining whether the pre-ejection period increases above a predetermined numerical threshold, wherein determining whether the left ventricular ejection time decreases comprises one of determining whether the left ventricular ejection time decreases by greater than a predetermined percentage over a predetermined number of days and determining whether the left ventricular ejection time decreases above a predetermined numerical threshold, and wherein determining whether the ratio of the pre-ejection period increases comprises one of determining whether the ratio of the pre-ejection period and the left ventricular ejection time increases by greater than a predetermined percentage over a predetermined number of days and determining whether the ratio of the pre-ejection period and the left ventricular ejection time increases above a predetermined numerical threshold.

Embodiment 18. The device of any of embodiments 11-17, wherein the processor is configured to determine trend data associated with the pre-ejection period, the left ventricular ejection time and a ratio of the pre-ejection period and the left ventricular ejection time for a plurality of the sensed cardiac events, determine whether the pre-ejection period is increasing, determine whether the left ventricular ejection time is decreasing; determine whether the ratio of the pre-ejection period and the left ventricular ejection time is increasing, determine whether heart failure is indicated in response to determining at least two of the pre-ejection period determined to be increasing, the left ventricular ejection time determined to be decreasing, and the ratio of the pre-ejection period and the left ventricular ejection time determined to be increasing, adjust delivery of the cardiac pacing therapy in response to one of determining the pre-ejection period is increasing and determining the ratio of the pre-ejection period and the left ventricular ejection time is increasing, and generate an alert in response to heart failure being indicated.

Embodiment 19. The device of any of embodiments 11-18, wherein determining whether the pre-ejection period increases comprises one of determining whether the pre-ejection period increases by greater than a predetermined percentage over a predetermined number of days and determining whether the pre-ejection period increases above a predetermined numerical threshold, wherein determining whether the left ventricular ejection time decreases comprises one of determining whether the left ventricular ejection time decreases by greater than a predetermined percentage over a predetermined number of days and determining whether the left ventricular ejection time decreases above a predetermined numerical threshold, and wherein determining whether the ratio of the pre-ejection period increases comprises one of determining whether the ratio of the pre-ejection period and the left ventricular ejection time increases by greater than a predetermined percentage over a predetermined number of days and determining whether the ratio of the pre-ejection period and the left ventricular ejection time increases above a predetermined numerical threshold.

Embodiment 20. The device of any of embodiments 11-19, wherein the cardiac pacing device comprises a leadless pacemaker device and the sensed pacing event comprises a ventricular pacing event.

Embodiment 21. A non-transitory computer readable medium storing instructions which cause a cardiac medical device to perform a method comprising:
delivering the cardiac pacing therapy from a cardiac pacing device;
sensing a pacing event from a plurality of electrodes of the pacing device;
sensing an electromechanical signal from an electromechanical sensor of the pacing device;
determining a pre-ejection period in response to the sensed electromechanical signal;
determining a left ventricular ejection time in response to the sensed electromechanical signal; and
performing one or both of adjusting a pacing parameter setting and generating an alert in response to the determined pre-ejection period and the determined left ventricular ejection time.

Embodiment 22. A medical device system comprising means to perform the method of any one of claims 1-10.

Embodiment 23. A computer-readable storage medium comprising instructions that, when executed by processing circuitry of a medical device system, cause the processing circuitry to perform the method of any of claims 1-10.

What is claimed:

1. A method of delivering a cardiac pacing therapy comprising:
   delivering the cardiac pacing therapy using a cardiac pacing device;
   sensing ventricular events using one or more electrodes of the cardiac pacing device over a predetermined number of days;
   sensing an electromechanical signal from an electromechanical sensor of the cardiac pacing device over the predetermined number of days;
   determining a pre-ejection period based on the sensed electromechanical signal for each sensing ventricular event over the predetermined number of days;
   determining a left ventricular ejection time based on the sensed electromechanical signal for each sensed ventricular event over the predetermined number of days;
   determining a ratio of the pre-ejection period and the left ventricular ejection time for each sensed ventricular event over the predetermined number of days; and
   determining heart failure worsening in response to at least two of the following:
   the determined pre-ejection period increasing by a PEP threshold or a PEP percentage over the predetermined number of days;
   the determined left ventricular ejection time decreasing by a LVET threshold or a LVET percentage over the predetermined number of days; and
   the determined ratio of the pre-ejection period and the left ventricular ejection time increasing by ratio threshold or a ratio percentage over the predetermined number of days.

2. The method of claim 1, wherein the electromechanical sensor comprises an accelerometer.

3. The method of claim 1, wherein the predetermined number of days is 5 days.

4. The method of claim 1, wherein the cardiac pacing device comprises a leadless pacemaker device.

5. The method of claim 1, the method further comprising adjusting delivery of the cardiac pacing therapy in response to determining heart failure worsening.

6. The method of claim 1, the method further comprising generating an alert in response to determining heart failure worsening.

7. The method of claim 1, wherein at least one of the PEP percentage, LVET percentage, and the ratio percentage is 20%.

8. The method of claim 1, wherein the PEP threshold is 400 milliseconds, the LVET threshold is 150 milliseconds, and the ratio threshold is 0.5.

9. The method of claim 1, the method further comprising:
determining cardiac dyssynchrony based on one or more of the determined pre-ejection period, the determined left ventricular ejection time, and the determined ratio of the pre-ejection period and the left ventricular ejection time; and
adjusting a pacing parameter setting of the cardiac pacing therapy in response to determining cardiac dyssynchrony.

10. The method of claim 9, wherein adjusting the pacing parameter setting of the cardiac pacing therapy in response to determining cardiac dyssynchrony comprises adjusting the pacing parameter setting of the cardiac pacing therapy on a cycle-by-cycle basis until one or more of the determined pre-ejection period, the determined left ventricular ejection time, and the determined ratio of the pre-ejection period and the left ventricular ejection time do not indicate dyssynchrony.

11. A cardiac pacing device to deliver cardiac pacing therapy comprising:
a processor operatively coupled to one or more electrodes and an electromechanical sensor, the processor configured to:
deliver the cardiac pacing therapy using the one or more electrodes;
sense ventricular events using the one or more electrodes over a predetermined number of days;
sense an electromechanical signal using the electromechanical sensor over the predetermined number of days;
determine a pre-ejection period based on the sensed electromechanical signal for each sensing ventricular event over the predetermined number of days;
determine a left ventricular ejection time based on the sensed electromechanical signal for each sensed ventricular event over the predetermined number of days;
determine a ratio of the pre-ejection period and the left ventricular ejection time for each sensed ventricular event over the predetermined number of days; and
determine heart failure worsening in response to at least two of the following:
the determined pre-ejection period increasing by a PEP threshold or a PEP percentage over the predetermined number of days;
the determined left ventricular ejection time decreasing by a LVET threshold or a LVET percentage over the predetermined number of days; and
the determined ratio of the pre-ejection period and the left ventricular ejection time increasing by ratio threshold or a ratio percentage over the predetermined number of days.

12. The device of claim 11, wherein the electromechanical sensor comprises an accelerometer.

13. The device of claim 11, wherein the predetermined number of days is 5 days.

14. The device of claim 11, wherein the cardiac pacing device comprises a leadless pacemaker device, wherein the leadless pacemaker device comprises a housing, wherein the one or more electrodes are coupled to the housing and the processor is located within the housing.

15. The device of claim 11, the processor is further configured to adjust delivery of the cardiac pacing therapy in response to determining heart failure worsening.

16. The device of claim 11, the processor is further configured to generate an alert in response to determining heart failure worsening.

17. The device of claim 11, the processor is further to:
determine cardiac dyssynchrony based on one or more of the determined pre-ejection period, the determined left ventricular ejection time, and the determined ratio of the pre-ejection period and the left ventricular ejection time; and
adjust a pacing parameter setting of the cardiac pacing therapy in response to determining cardiac dyssynchrony.

18. The device of claim 17, wherein adjusting the pacing parameter setting of the cardiac pacing therapy in response to determining cardiac dyssynchrony comprises adjusting the pacing parameter setting of the cardiac pacing therapy on a cycle-by-cycle basis until one or more of the determined pre-ejection period, the determined left ventricular ejection time, and the determined ratio of the pre-ejection period and the left ventricular ejection time do not indicate dyssynchrony.

19. A cardiac pacing device to deliver cardiac pacing therapy comprising:
a processor operatively coupled to one or more electrodes and an electromechanical sensor, the processor configured to:
deliver the cardiac pacing therapy using the one or more electrodes;
sense ventricular events using the one or more electrodes over a predetermined number of days;
sense an electromechanical signal using the electromechanical sensor over the predetermined number of days;
determine a pre-ejection period based on the sensed electromechanical signal for each sensing ventricular event over the predetermined number of days;
determine a left ventricular ejection time based on the sensed electromechanical signal for each sensed ventricular event over the predetermined number of days;
adjust a pacing parameter setting of the cardiac pacing therapy in response to the determined pre-ejection period increasing by a PEP threshold or a PEP percentage over the predetermined number of days; and
determine heart failure worsening in response to the determined pre-ejection period increasing by a PEP threshold or a PEP percentage over the predetermined number of days and the determined left ventricular ejection time decreasing by a LVET threshold or a LVET percentage over the predetermined number of days.

20. The device of claim 19, wherein the processor is further configured to:

determine a ratio of the pre-ejection period and the left ventricular ejection time for each sensed ventricular event over the predetermined number of days in response to determining no heart failure worsening;

adjust the pacing parameter setting of the cardiac pacing therapy in response to the determined ratio of the pre-ejection period and the left ventricular ejection time increasing by ratio threshold or a ratio percentage over the predetermined number of days; and determine heart failure worsening in response to the determined pre-ejection period increasing by a PEP threshold or a PEP percentage over the predetermined number of days or the determined left ventricular ejection time decreasing by a L VET threshold or a LVET percentage over the predetermined number of days following the adjusting the pacing parameter setting.

* * * * *